Figure 1:
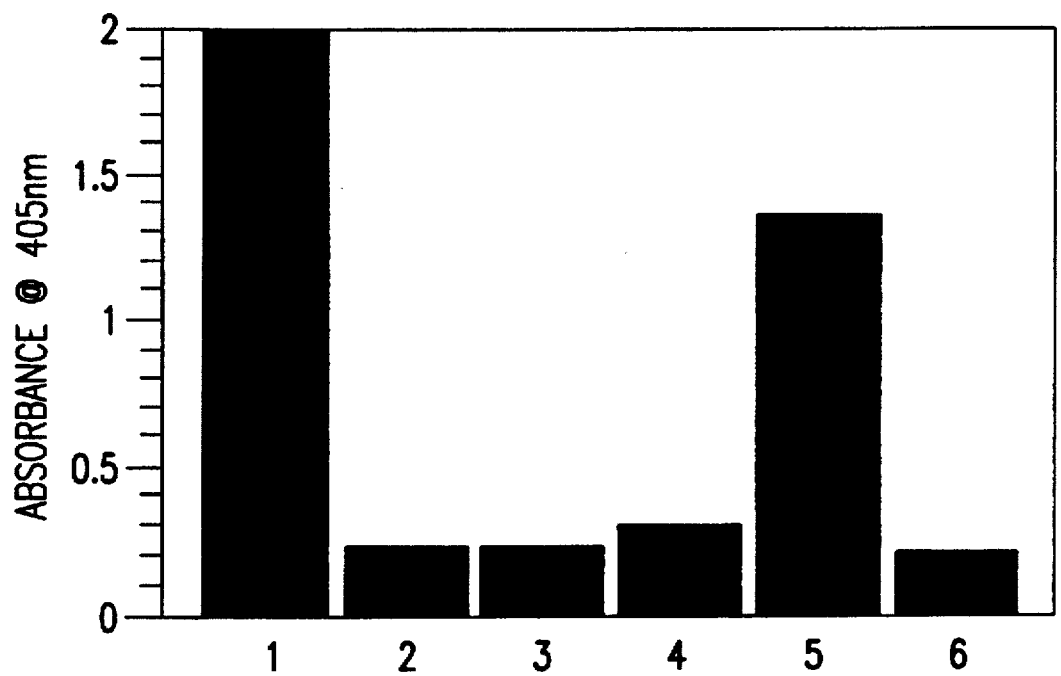
Figure 2:
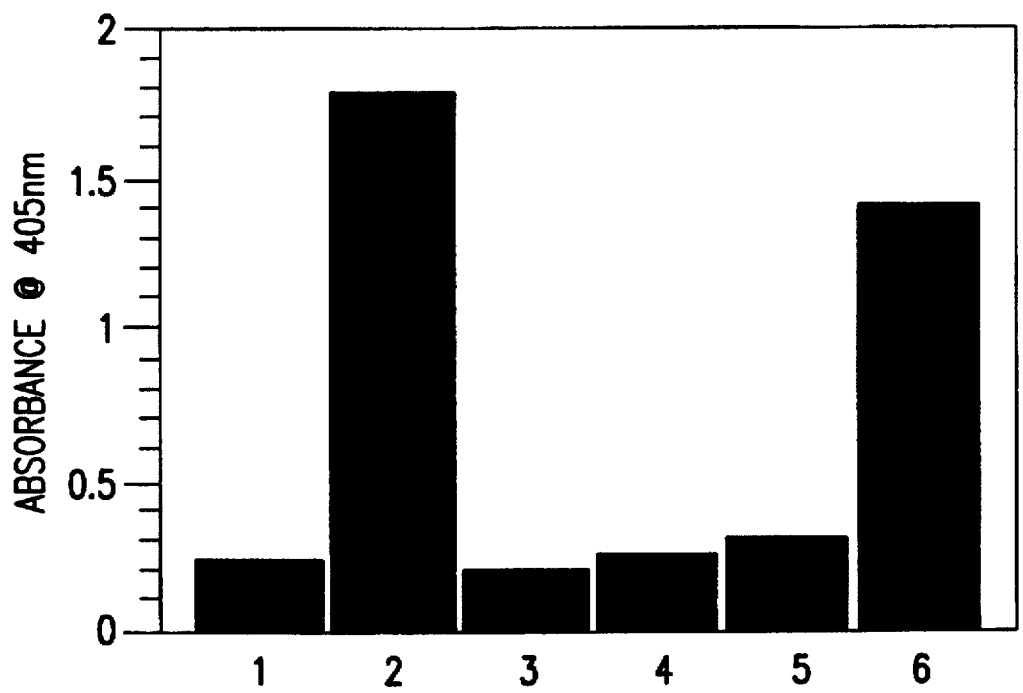
Figure 3:
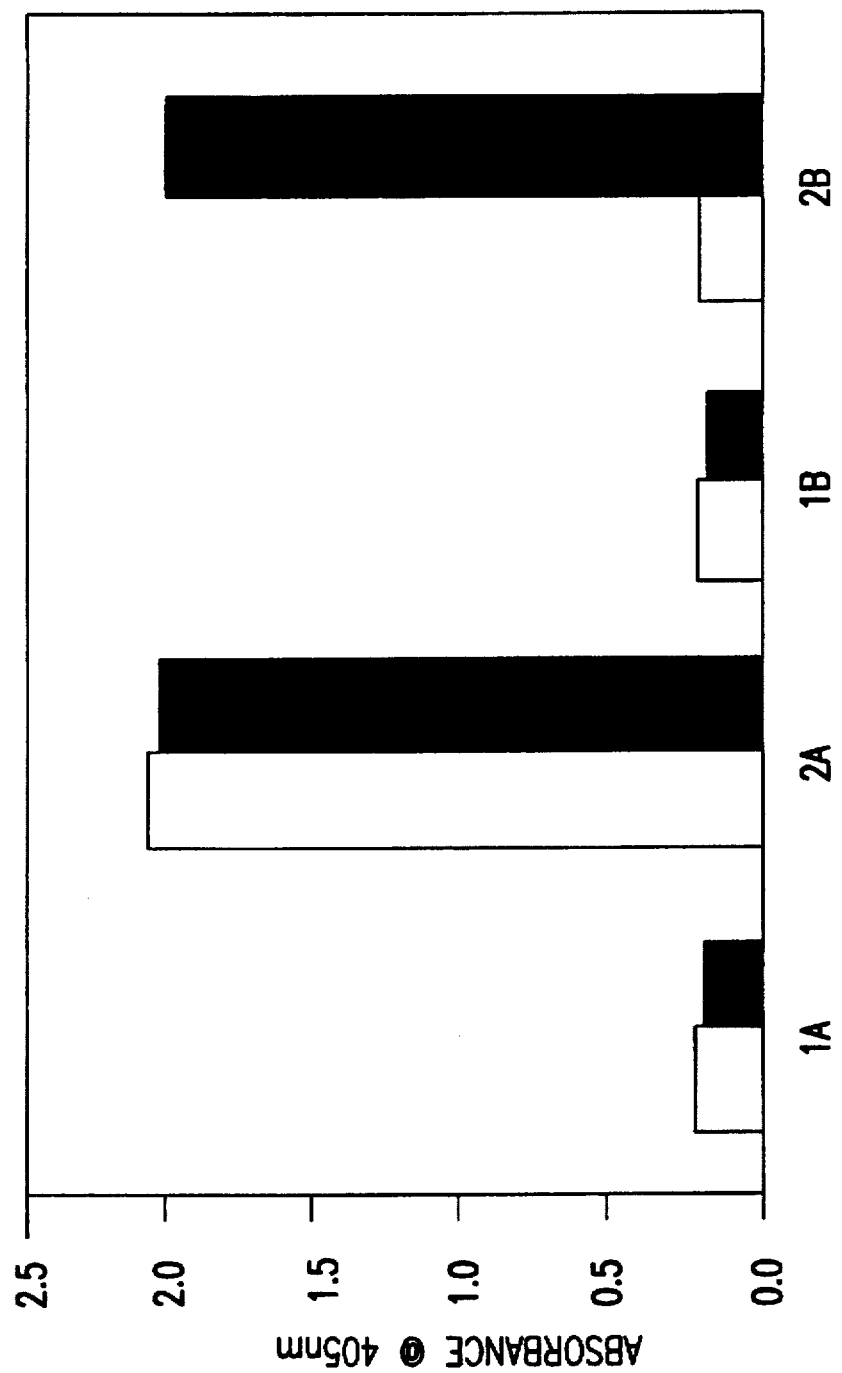
Figure 5:
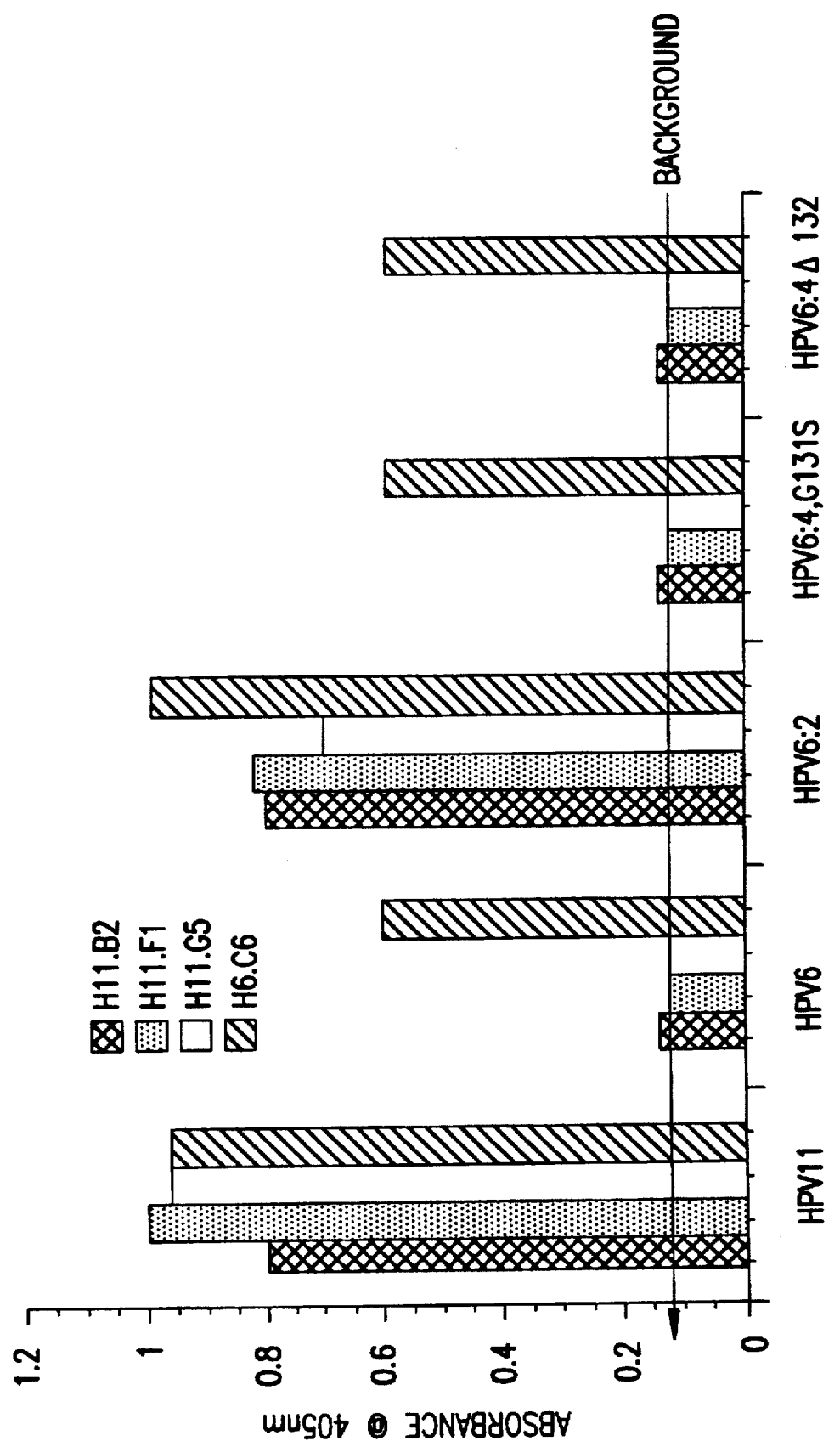

United States Patent [19]

Ludmerer et al.

[11] Patent Number: 5,738,853
[45] Date of Patent: Apr. 14, 1998

[54] SYNTHETIC HPV11 VIRUS-LIKE PARTICLES

[75] Inventors: Steven Ludmerer, Picataway; George E. Mark, III, Princeton Junction; Diana Benincasa, Elizabeth, all of N.J.

[73] Assignee: Merck & Co., Inc., Rahway, N.J.

[21] Appl. No.: 738,509

[22] Filed: Oct. 24, 1996

Related U.S. Application Data

[60] Provisional application No. 60/006,788, Nov. 15, 1995.

[51] Int. Cl.$^6$ .................. A61K 39/12; A61K 39/395; C12N 15/00; A01N 37/18
[52] U.S. Cl. .................. 424/204.1; 424/178.1; 424/184.1; 424/94.1; 424/205.1; 435/172.3; 435/5; 435/7.14; 435/7.924; 536/23.72; 514/2
[58] Field of Search .................. 424/201.1, 178.1, 424/184.1, 94.1, 205.1; 435/172.3, 5, 7.14, 7.924; 536/23.72; 514/2

[56] References Cited

PUBLICATIONS

Christensen et al, 1994, Virology, vol. 205, pp. 329–335.
Dako Corp., 1993 Catalog, p. 119, Code 486.
Christensen, et al., "Antibody–Mediated Neutralization In Vivo of Infectious Papillomaviruses", J. Virol., 64, pp. 3151–3156 (1990).
Christensen, et al., "Monoclonal Antibody–Mediated Neutralization of Infectious Human Papillomavirus Type 11", J. Virol., 64, pp. 5678–5681 (1990).
Rose, et al., "Expression of Human Papillomavirus Type 11 L1 Protein in Insect Cells: InVivo and In Vitro Assembly of Viruslike Particles", J. Virol., 67, pp. 1936–1944 (1993).
Rose, et al., "Human papillomavirus (HPV) type 11 recombinant virus–like particles induce the formation of neutralizing antibodies . . . ", J. Gen. Virol., 72, pp. 2075–2079 (1994).
Christensen, et al., "Assembled baculovirus–expressed human papillomavirus type 11 L1 capsid protein virus–like particles . . . ", J. Gen. Virol. 75, pp. 2271–2276 (1994).

Primary Examiner—Marian C. Knode
Assistant Examiner—Ali R. Salimi
Attorney, Agent, or Firm—Joanne M. Giesser; Jack L. Tribble

[57] ABSTRACT

The present invention is a series of synthetic virus-like particles useful in the characterization of human papillomavirus infection and assays employing the synthetic virus-like particles. The synthetic virus-like particles are generated from constructs designated as HPV6:4; HPV6:5; HPV6:2; HPV6:4Δ132; and HPV6:4,S131G.

1 Claim, 4 Drawing Sheets

```
HPV11     ---------------------------------------------K----------------Y--KV------    4
HPV6b     ---------------------------------------------T----------------F--RA------    4

CONSENSUS MWRPSDSTVYVPPPNPVSKVVATDAYV-RTNIFYHASSRLLAVGHPY-SIK--NKTVVPKVSGYQYRVFKVVLPDPNKFALPDSSLFDPTTQRLVWACT  100

HPV11     -------------------L--------------GY-----------------------------T-S-S--N-------   11
HPV6b     -------------------F----------------S------------------------------K-T-P--A-----   10

CONSENSUS GLEVGRGQPLGVGVSGHP-LNKYDDVENSG--GGNPGQDNRVNVGMDYKQTQLCMVGCAPPLGEHWGKG-QC-NT-VQ-GDCPPLELITSVIQDGDMVDT  200

HPV11     --------L-------V----------------Y------T--------D-LV--GN-S-A---H---   23
HPV6b     --------I-------T----------------F------E------T-II--SG--T-G---N---   22

CONSENSUS GFGAMNFADLQTNKSDVP-DICGT-CKYPDYLQMAADPYGDRLFF-LRKEQMFARHFFNRAG-VGEPVPD-L--KG--NR-SV-SSIYV-TPSGSLVSSE  300

HPV11     ------H----SK-A------F--   28
HPV6b     ------Q----TT-S------Y--   27

CONSENSUS AQLFNKPYWLQKAQGHNNGICWGN-LFVTVVDTTRSTNMTLCASV--S-TYTNSDYKEYMRHVEE-DLQFIFQLCSITLSAEVMAYIHTMNPSVLEDWNF  400

HPV11     ------Q---DM--------F------T-A---I---P-T-   38
HPV6b     ------P---NL--------Y------S-I---V---A-A-   37

CONSENSUS GLSPPPNGTLEDTYRYVQSQAITCQKPTPEKEK-DPYK--SFWEVNLKEKFSSELDQ-PLGRKFLLQSGYRGR-S-RTG-KRPAVSK-S-APKRKR-KTK  500

HPV11     K   39
HPV6b     R   38

CONSENSUS -   501
```

FIG. 4

1

SYNTHETIC HPV11 VIRUS-LIKE PARTICLES

CROSS-REFERENCE TO RELATED APPLICATIONS

Not applicable.

STATEMENT REGARDING FEDERALLY-SPONSORED R&D

This application claims priority from U.S. Provisional application Ser. No. 60/006,788, filed Nov. 15, 1995.

REFERENCE TO MICROFICHE APPENDIX

Not applicable.

FIELD OF THE INVENTION

The present invention is a series of synthetic virus-like particles (VLP) useful in the characterization of human papillomavirus infection and assays employing the synthetic virus-like particles.

BACKGROUND OF THE INVENTION

Papillomavirus infections occur in a variety of animals, including humans, sheep, dogs, cats, rabbits, monkeys, snakes and cows. Papillomaviruses infect epithelial cells, generally inducing benign epithelial or fibroepithelial tumors at the site of infection. Papillomaviruses are species specific infective agents; a human papillomavirus cannot infect a nonhuman animal.

Papillomaviruses may be classified into distinct groups based on the host that they infect. Human papillomaviruses (HPV) are further classified into more than 60 types based on DNA sequence homology (for a review, see Papillomaviruses and Human Cancer, H. Pfister (ed.), CRC Press, Inc., 1990). Papillomavirus types appear to be type-specific immunogens in that a neutralizing immunity to infection to one type of papillomavirus does not confer immunity against another type of papillomavirus.

In humans, different HPV types cause distinct diseases. HPV types 1, 2, 3, 4, 7, 10 and 26-29 cause benign warts in both normal and immunocompromised individuals. HPV types 5, 8, 9, 12, 14, 15, 17, 19-25, 36 and 46-50 cause flat lesions in immunocompromised individuals. HPV types 6, 11, 34, 39, 41-44 and 51-55 cause nonmalignant condylomata of the genital or respiratory mucosa. HPV types 16 and 18 cause epithelial dysplasia of the genital mucosa and are associated with the majority of in situ and invasive carcinomas of the cervix, vagina, vulva and anal canal. HPV6 and HPV11 are the causative agents for more than 90% of all condyloma (genital warts) and laryngeal papillomas. The most abundant subtype of HPV type 6 is HPV6a.

Immunological studies in animals have shown that the production of neutralizing antibodies to papillomavirus antigens prevents infection with the homologous virus. The development of effective papillomavirus vaccines has been slowed by difficulties associated with the cultivation of papillomaviruses in vitro. The development of an effective HPV vaccine has been particularly slowed by the absence of a suitable animal model. Neutralization of papillomavirus by antibodies appears to be type-specific and dependent upon conformational epitopes on the surface of the virus.

Papillomaviruses are small (50-60 nm), nonenveloped, icosahedral DNA viruses that encode for up to eight early and two late genes. The open reading frames (ORFs) of the virus genomes are designated E1 to E7 and L1 and L2, where "E" denotes early and "L" denotes late. L1 and L2 code for virus capsid proteins. The early (E) genes are associated with functions such as viral replication and cellular transformation.

The L1 protein is the major capsid protein and has a molecular weight of 55-60 kDa. L2 protein is a minor capsid protein which has a predicted molecular weight of 55-60 kDa and an apparent molecular weight of 75-100 kDa as determined by polyacrylamide gel electrophoresis. Immunologic data suggest that most of the L2 protein is internal to the L1 protein. The L2 proteins are highly conserved among different papillomaviruses, especially the 10 basic amino acids at the C-terminus. The L1 ORF is highly conserved among different papillomaviruses.

The L1 and L2 genes have been used to generate vaccines for the prevention and treatment of papillomavirus infections in animals. Zhou et al., (1991; 1992) cloned HPV type 16 L1 and L2 genes into a vaccinia virus vector and infected CV-1 mammalian cells with the recombinant vector to produce virus-like particles (VLP).

Bacterially-derived recombinant bovine papillomavirus L1 and L2 have been generated. Neutralizing sera to the recombinant bacterial proteins cross-reacted with native virus at low levels, presumably due to differences in the conformations of the native and bacterially-derived proteins.

Recombinant baculoviruses expressing HPV6 L1, HPV11 L1, HPV16 L1, HPV18 L1, HPV31 L1 or HPV16 L2 ORFs have been used to infect insect Sf9 cells and produce L1 and L2 proteins. Western blot analyses showed that the baculovirus-derived L1 and L2 proteins reacted with antibody to HPV16. The baculovirus derived L1 forms VLPs.

Carter et al., (1991) demonstrated the production of HPV16 L1 and HPV16 L2 proteins by recombinant strains of *Saccharomyces cerevisiae*. Carter et al. also demonstrated the production of HPV6b L1 and L2 proteins. The HPV6b L1 protein was not full-length L1 protein. The recombinant proteins were produced as intracellular as well as secreted products. The recombinant L1 and L2 proteins were of molecular weights similar to the native proteins. When the proteins were expressed intracellularly, the majority of the protein was found to be insoluble when the cells were lysed in the absence of denaturing reagents. Although this insolubility may facilitate purification of the protein, it may hamper analysis of the native epitopes of the protein.

Recombinant proteins secreted from yeast were shown to contain yeast-derived carbohydrates. The presence of these N-linked oligosaccharides may mask native epitopes. In addition, the secreted recombinant proteins may contain other modifications, such as retention of the secretory leader sequence.

The present invention is directed to the production of recombinant papillomavirus proteins having the immunity-conferring properties of the native papillomavirus proteins as well as methods for their production and use. The present invention is a series of synthetic virus-like particles useful in the characterization of human papillomavirus infection and assays employing the synthetic virus-like particles.

The invention involves the delineation of residues specific to HPV11 L1 which are required for binding neutralizing antibodies. The invention further involves the delineation of two residues specific to HPV11 L1 which together are necessary and sufficient for binding neutralizing antibodies.

HPV11 L1 contains only 38 amino acid differences from HPV6 L1, plus one residue insertion. In spite of the strong identity between these two proteins, a panel of neutralizing monoclonal antibodies which are specific for HPV11 VLPs has been generated. We determined which of these amino acid positions are important for the binding of the neutralizing monoclonal antibodies. This was accomplished by assessing binding of the monoclonal antibodies to a family of HPV11 clones which contained substitutions of HPV6b amino acid residues for HPV11 amino acid residues at these positions, and then mutating HPV6b to match the HPV11 sequence at these critical positions. We demonstrated that the neutralizing antibodies will bind HPV6b VLPs with as few as two of these substitutions, and that both substitutions are essential for binding. This work defines the minimal unit for binding neutralizing antibodies.

The panel of neutralizing monoclonal antibodies for HPV11 was obtained from Neil Christiansen (Pennsylvania State University, Hershey, Pa.). The monoclonal antibodies in the panel are HPV11 specific and VLP-dependent. The antibodies may be distinguished from each other in terms of which amino acid residues affect binding of the individual antibodies, although there are overlapping positions for all the monoclonal antibodies.

These residues collectively define the epitope for antibodies known to neutralize HPV11. In principle, the mutation of HPV6 L1 in only these select positions results in binding to these HPV11 specific neutralizing monoclonal antibodies. The derivatized HPV6 VLPs may be used to generate monoclonal antibodies to the HPV11 neutralizing epitope. This is the basis of a release assay to verify that manufactured HPV11 VLPs contain the neutralizing epitope.

This problem has not been solved in the past and, to our knowledge, is the first demonstration of the transfer of a conformationlly dependent epitope.

There were two difficulties to overcome. First, the epitope is conformational, and conventional means of epitope mapping, binding to peptide fragments, could not be utilized. It was necessary to express any test L1 protein in a way that facilitated formation of virus-like particles which mimic the virus structure. Second, the large number of L1 clones required for the mapping necessitated the generation of a facile means to express the test viral coat proteins.

Without knowledge of the neutralizing epitope, it would be difficult to validate manufacture of VLPs for commercial use.

One use of the derivatized VLP is as a reagent in a release assay to HPV11. HPV6 L1 is mutated to match HPV11 in the positions defined by these studies. Binding of the HPV11 neutralizing monoclonal antibodies to these derivatized HPV6 VLPs will be demonstrated.

These derivatized HPV6 VLPs may be used in a competition binding assay with manufactured HPV11 VLPs for binding to the HPV11 neutralizing monoclonal antibodies. Only those HPV6 derivatives demonstrated to bind the monoclonal antibodies will compete with authentic material.

Alternatively, monoclonal antibodies may be generated to the neutralizing epitope on derivatized HPV6; then manufactured HPV11 vaccine will be demonstrated to bind these antibodies.

SUMMARY OF THE INVENTION

The present invention is a series of synthetic virus-like particles useful in the characterization of human papillomavirus infection and assays employing the synthetic particles. The synthetic virus-like particles are generated from constructs designated as HPV6:4; HPV6:5; HPV11:G131S; HPV11 :Δ132; HPV11Y246F; HPV11:N278G; HPV11:S346T; HPV6:2; HPV6:4Δ132; and HPV6:4, S131G.

BRIEF DESCRIPTION OF THE DRAWINGS

FIG. 1 shows VLPs with type-specific properties are generated in transient transfection. Sf9 cells were cotransfected with Baculogold™ DNA and either pVL1393:CRPV or pVL1393:HPV11. Cells were harvested after six days, extracts prepared, and ELISAs performed as described in the text. Column 1, CRPV VLPs; column 2, HPV11 VLPs; column 3, SF9 extract; column 4, baculovirus DNA; column 5, pVL1393:CRPV; column 6, pVL1393:HPV11.

The primary antibody is $10^{-5}$ dilution of CRPV.5A ascites fluid.

FIG. 2 shows the same experiment as FIG. 1, except that the primary antibody is $10^{-5}$ dilution of H11.F1 ascites fluid.

FIG. 3 shows the immunogenic material produced by transient transfection is sensitive to denaturation. Sf9 cells were cotransfected with pVL1393:HPV11 and BaculoGold™ DNA, cells were harvested after six days, and extracts prepared as described in the text. A portion of the extracts were denatured by dilution into 0.1M Sodium Carbonate, pH 10.5, and incubated at room temperature for 1 hour. These extracts were then coated onto a microtiter plate and allowed to dry. Untreated extracts were coated onto microtiter plates and incubated overnight at 4° C. ELISAs were performed as described in Methods using a $10^{-5}$ dilution of either H11.F1 or H6.C6 ascites. Column 1, Sf9 extract; column 2, pVL1393 extract. A, extract is non-denatured. B, extract was carbonate buffer treated.

FIG. 4 shows the amino acid sequences of the HPV11 and HPV6 L1 protein. These sequences are also available in the EMBL Gene Bank.

FIG. 5 shows that VLPs produced from clone HPV6:2 (with a substitution at position 131, followed by the tyrosine insertion to create position 132) binds antibodies H11.B2, H11.F1 and H11.G5. In contrast, VLPs produced from HPV6:4 back-mutated at either position 131 (HPV6:4, G131S) or 132 (HPV6:4Δ132) do not bind these antibodies, in spite of the presence of the three other critical residue changes. Antibodies H11B2, H11F1 and H11G5 are neutralizing MAbs in the xenograft system. H6C6 measures the total level of L1 production as described in Example 4. The ELISA was performed as described in Example 3.

DETAILED DESCRIPTION OF THE INVENTION

The present invention is a series of synthetic virus-like particles (VLP) useful in the characterization of human papillomavirus infection and assays employing the synthetic virus-like particles, which may be used to monitor and validate VLPs manufactured through recombinant DNA technologies. The synthetic virus-like particles are generated from constructs designated as HPV6:4; HPV6:5; HPV11:G131S; HPV11:Δ132; HPV11Y246F; HPV11:N278G; HPV11:S346T; HPV6:2; HPV6:4Δ132; and HPV6:4,S131G.

Papillomavirus infections occur in a variety of animals, including humans, sheep, dogs, cats, rabbits, monkeys, snakes and cows. Papillomaviruses infect epithelial cells, generally inducing benign epithelial or fibroepithelial tumors at the site of infection.

Papillomaviruses may be classified into distinct groups based on the host that they infect. Human papillomaviruses (HPV) are further classified into more than 60 types based on DNA sequence homology (for a review, see Papillomaviruses and Human Cancer, H. Pfister (ed.), CRC Press, Inc., 1990). Papillomavirus types appear to be type-specific immunogens in that a neutralizing immunity to infection to one type of papillomavirus does not confer immunity against another type of papillomavirus.

In humans, different HPV types cause distinct diseases. HPV types 1, 2, 3, 4, 7, 10 and 26–29 cause benign warts in both normal and immunocompromised individuals. HPV types 5, 8, 9, 12, 14, 15, 17, 19–25, 36 and 46–50 cause flat lesions in immunocompromised individuals. HPV types 6, 11, 34, 39, 41–44 and 51–55 cause nonmalignant condylomata of the genital and respiratory mucosa. HPV types 16 and 18 cause epithelial dysplasia of the genital tract and are associated with the majority of in situ and invasive carcinomas of the cervix, vagina, vulva and anal canal. HPV6 and HPV11 cause the majority of genital warts and laryngeal papillomas.

Immunological studies in animals have shown that the production of neutralizing antibodies to papillomavirus capsid proteins prevents infection with the homologous virus. The development of effective papillomavirus vaccines has been slowed by difficulties associated with the cultivation of papillomaviruses in vitro. The development of an effective HPV vaccine has been particularly slowed by the absence of a suitable animal model. Neutralization of papillomavirus by antibodies appears to be type-specific and dependent upon conformational epitopes on the surface of the virus.

Papillomaviruses are small (50–60 nm), nonenveloped, icosahedral DNA viruses that encode for up to eight early and two late genes. The open reading frames (ORFs) of the virus genomes are designated E1 to E7 and L1 and L2, where "E" denotes early and "L" denotes late. L1 and L2 code for virus capsid proteins. The early (E) genes are associated with functions such as viral replication and transformation.

The L1 protein is the major capsid protein and has a molecular weight of 55–60 kDa. L2 protein is a minor capsid protein which has a predicted molecular weight of 55–60 kDa and an apparent molecular weight of 75–100 kDa as determined by polyacrylamide gel electrophoresis.

The production of HPV 16 L1, HPV16 L2, and HPV type 6 L1 proteins by recombinant strains of Saccharomyces cerevisiae has been reported. It would be useful to develop methods of producing large quantities of papillomavirus proteins of any species and type by cultivation of recombinant yeasts. It would also be useful to produce large quantities of papillomavirus proteins having the immunity-conferring properties of the native proteins, such as the conformation of the native protein. To achieve this latter goal it would be necessary to analyze the effect of numerous mutations in th L1 gene on the binding of antibodies of known properties (VLP dependent, cross-reactive, etc.)

The empirical scanning of natural or engineered peptide sequences for functional residues is inherently dependent upon expression of large numbers of sequence variants to assay their relative functional potency. The level of protein expression obtained can be particularly critical in the case of self-assembling viral structural proteins, because the efficiency of self-assembly frequently is concentration dependent. The insect baculovirus expression vector system has been widely used to study viral self-assembly, but it generally requires prior isolation and expansion of a plaque-purified recombinant viral stock to generate useful quantities of self-assembled particles. In examining a number of possibilities for expression of analytical levels of the L1 coat protein of Cottontail Rabbit and Human Type 11 Papillomaviruses, we found that even brief transient cotransfection of insect cells with baculovirus transfer vectors and viral DNA yielded assembled particles which were immunologically indistinguishable from particles previously obtained from plaque purified stocks. Within six days of plasmid/viral DNA cotransfection of Sf9 cells, at least 1–2 μg of assembled L1 particles/100 mm plate could be demonstrated. This level of expression is more than sufficient to assay functionality, and has several advantages over comparable mammalian cell transient expression systems.

To define neutralizing epitopes in HPV infections, we need to identify the amino acid residues that confer antigenic type-specificity on human papillomavirus subtypes (Christensen, N. D., et al., 1990,. Monoclonal antibody-mediated neutralization of infectious human papillomavirus type 11. *J. Virol.* 64, 1936–1944). Many of the type-specific epitopes are conformationally-dependent and are detectable only upon VLP assembly. The L1 structural coat protein of several animal and human papillomaviruses has been demonstrated to efficiently self-assemble when expressed in insect cells via recombinant baculovirus strains (Christensen, N. D., et al., 1994, Assembled baculovirus-expressed human papillomavirus type 11 L1 capsid protein virus-like particles are recognized by neutralizing monoclonal antibodies and induce high titres of neutralizing antibodies. J. Gen. Virol. 75, 2271–2276). The time and labor involved in the generation of recombinant phage precludes the use of this method to screen a large number of VLP variants produced through site-directed mutagenesis. However, we previously observed that when expressed in the baculovirus system, a recombinant protein is detectable as a secreted product in μg/ml quantities within 5–7 days of the initial transfection of insect cells with plasmid and viral DNAs. Based upon this observation, we examined whether sufficient quantities of papillomavirus L1 protein would accumulate to allow self-assembly into VLPs upon transient expression, particularly if a more efficient baculovirus transfection system such as the Baculogold™ (Pharmingen, San Diego, Calif.) system were utilized. Employing a rapid 6-day transient transfection protocol, the L1 coat protein of of numerous papillomavirus types, properly assembled into VLPs, was produced. Extracts prepared from transiently transfected cells with CRPV or HPV11 L1 gene constructs contained immunogenic material recognized by type-specific and VLP dependent monoclonal antibodies generated against either CRPV or HPV11 VLPs. The transiently expressed material was not cross-reactive with other type-specific antibodies, and recognition was sensitive to alkaline denaturation, further demonstrating fidelity in VLP formation.

To map the HPV11 neutralizing epitope, we individually mutated HPV11 at the residues where the sequence diverges from the HPV6b sequence. The positions were mutated to match the HPV6b sequence (the tyrosine at position 132 was deleted to analyze the effect of this insertion). Using the Sf9 transient expression system described above, these mutant HPV11 L1 genes were expressed and analyzed for binding by HPV11 specific monoclonal antibodies.

The following examples are provided to further define the invention without, however, limiting the invention to the particulars of these examples.

EXAMPLE 1

Generation of test expression constructs.

The HPV11 L1 structural gene was cloned from clinical isolates using PCR with primers designed from the published L1 sequence. The L1 gene was subsequently subcloned both into BlueScript (Pharmacia) for mutagenesis, and pVL1393 (Stratagene) for expression in Sf9 cells.

Mutations were introduced into the L1 gene using Amersham Scultor in vitro mutagenesis kit. The appearance of the desired mutation was confirmed by sequencing, and the mutated gene subcloned into pVL1393 for expression in Sf9 cells.

The HPV6 L1 structural gene was subcloned both into pAlt-1 (Promega) for mutagenesis, and pVL1393 (Stratagene) for expression in Sf9 cells. Mutations were generated using the Altered Sites II in vitro mutagenesis Systems (Promega), verified by sequencing, and subcloned into pVL1393 for expression in Sf9 cells.

Sequences of the L1 genes of HPV6 and HPV11 were verified with the published sequences. [(Dartmann, K., et al. 1993, EMBO J. 2: 2341; EMBL GeneBank Accession #M14119 (HPV11 L1) and Accession #X00203 (HPV6B L1)].

EXAMPLE 2

Transient Expression of L1 VLPs in SF9 cells.

SF9 cells were transfected using BaculoGold Transfection kit (Pharmingen). Transfections were done essentially according to the manufacturer's instructions with the following modifications. $8 \cdot 10^8$ Sf9 cells were transfected in a 100 mM dish, with 4 µg of BaculoGold DNA and 6 ug of test DNA. Cells were harvested after 6 days and assayed for VLP production.

EXAMPLE 3

Preparation of SF9 extracts and ELISA assays.

Cells were harvested six days after transfection, by scraping followed by low speed centrifugation. Cells were resuspended in 300 µl of breaking buffer (1M NaCl, 0.2M Tris pH 7.6) and homogenized for 30" on ice using a Polytron PT 1200 B with a PT-DA 1205/2-A probe (Brinkman) in a Falcon 1259 tube. Samples were spun at 2500 rpm for 3 minutes to pellet debris. Tubes were washed with an additional 150 µl of breaking buffer, supernatents collected in a 1.5 ml microfuge tube, and respun for 5 minutes in an Eppendorf microfuge (Brinkman). Supernatants were collected and stored at 4° C. until use. ELISA assays typically were performed the same day.

5 µl of extract was diluted into 50 µl of 1% BSA in PBS (phosphate buffered saline; 20 mM NaPO$_4$, pH 7.0, 150 mM NaCl) and plated onto a polystyrene plate. The plate was incubated overnight at 4° C. Extracts were removed and the plate blocked with 5% powdered milk in PBS. All subsequent wash steps were performed with 1% BSA in PBS. The plate was incubated at room temperature with primary antibody for 1 hour. Primary antibodies, monoclonal antibodies generated against HPV11 VLPs, were obtained as ascites stock from Dr. Neil Christensen (Pennsylvania State University). They were diluted $10^5$ in 1% BSA PBS before use. After washing, plates were incubated for 1 hour with secondary antibody. The secondary antibody, peroxidase labeled Goat anti-Mouse IgG ($\gamma$), was purchased from Kirkegaard & Perry Laboratories, Inc. and used at $10^3$ dilution in 1% BSA in PBS. After a final washing, a horseradish peroxidase assay was performed and absorbance read at 405 nm.

EXAMPLE 4

HPV11 scan

To map the residues critical for an HPV11 specific neutralizing epitope, we take advantage of two conditions. First of all, we used a panel of monoclonal antibodies which are specific for HPV11 L1 and recognize L1 only when in a VLP. The assay conditions described in Example 3 are such that these antibodies are non-cross-reactive to the closely related HPV6b L1 VLP. Among these five antibodies, 4 have been demonstrated to neutralize HPV 11 in the Kreider Xenograft system (Kreider et al., 1987, J. Virol. 61: 590–593)

HPV6 and HPV11 L1s are the most closely related L1 proteins within the papilloma virus family. HPV6 L1 is 500 amino acid residues in length. HPV11 L1 is 501 residues. They can be aligned such that the extra amino acid in HPV11 is at position 132. With this alignment, they are identical in amino acid sequence in all but 39 positions (92.4%), including the insertion.

We reasoned that the type 11 specificity of the monoclonal antibodies must reside within these 39 residue differences. By systematically changing a type 11 residue into a type 6, those residues critical to the type 11 response would be revealed by a loss in binding affinity by the type 11 specific monoclonal antibodies. Because the residues would be mutated to residues which appear naturally in type 6, the likelihood of such substitutions affecting VLP formation would be small.

To determine the affect on binding of any particular residue, both HPV11 and the corresponding HPV11 derivative were expressed in the transient expression system. An ELISA was performed using the panel of HPV11 specific monoclonal antibodies, and results between the two compared. L1 production was normalized with monoclonal antibody H6.C6. H6.C6 antibody is cross-reactive with HPV11, the epitope is linear and independent of VLP formation. Thus it measures L1 production.

Results are put through a double normalization. First, the ratio of absorbance of the test antibody to H6.C6 is calculated for the test position. The same ratio is determined for HPV11 and divided into the ratio for the test position. Thus a double ratio near 1 means that there is no detectable difference in antibody binding to the test clone relative to HPV11. A double ratio less than one means that the test antibody binds more poorly to the test clone than wild-type. In theory, a ratio greater than 1 means that the antibody binds better to the test clone than to HPV11. In practice this was not observed. A ratio in the range of 0.1 to 0.2 is essentially background, meaning we cannot detect binding of the antibody to the mutant VLP.

The positions in HPV11 L1 which differ from HPV6 were individually mutated the match the corresponding residue in HPV6. Clones were expressed in SF9 cells through a Baculovirus expressing recombinant, and affect of binding by the panel of HPV11 specific monoclonal antibodies determined (Table 1). Residues which appear in column 2, labelled 'less binding', are positions deemed critical for binding one or more of the monoclonal antibodies. Residues listed in column 1, labeled 'retains binding', are judged not critical for binding any of the monoclonal antibodies.

TABLE 1

| Retains Binding | Loses Binding |
| --- | --- |
| HPV11:K28T | HPV11:G131S |
| HPV11:Y49F | HPV11:Y132Δ |

TABLE 1-continued

| Retains Binding | Loses Binding |
|---|---|
| HPV11:K53R | HPV11:Y246F |
| HPV11:V54A | HPV11:N278G |
| HPV11:L119F | HPV11:S346T |
| HPV11:T170K | |
| HPV11:S173T | |
| HPV11:S166P | |
| HPV11:N179A | |
| HPV11:L219I | |
| HPV11:V225T | |
| HPV11:T263E | |
| HPV11:D271T | |
| HPV11:L273I | |
| HPV11:V274I | |
| HPV11:G277S | |
| HPV11:S281T | |
| HPV11:A294G | |
| HPV11:H300N | |
| HPV11:H325Q | |
| HPV11:K347T | |
| HPV11:A349S | |
| HPV11:F366V | |
| HPV11:Q434P | |
| HPV11:D439N | |
| HPV11:M440L | |
| HPV11:F458Y | |
| HPV11:T474S | |
| HPV11:A467I | |
| HPV11:P488A | |
| HPV11:T497A | |

The clones which encode the L1 mutants described in Table 1 under the column 'loses binding' are designated HPV11:G13S, HPV11:Y132Δ, HPV11:Y246F, HPV11:N278G, and HPV11:S346T. Alternatively, the 'HPV' prefix may be omitted.

The four residues which affect binding are spaced at considerable distances from each other, with the total span encompassing greater than 200 residues along the linear sequence.

The positions affect the binding of the antibodies differentially. No more than three positions affect the binding of any single antibody. Only position 246 affects the binding of all five antibodies. In all cases, some measure of detectable binding is observed. This indicates that VLP formation is not affected. The affect on binding by the change at position 278 appears marginal and is questionable, but it is included at this time because the slight diminishment is reproducible. The affect on binding, as measured by the VLP normalized affinity ratio, is given in Table 2. Table 3 gives the binding configurations for the HPV11 monoclonal antibodies, as deduced from these studies.

TABLE 2

| | VLP Normalized Affinity Ratio* | | | | |
|---|---|---|---|---|---|
| Position | H11.A3.2 | H11.B2 | H11.F1 | H11.G5 | H11.F3 |
| G131S | 0.93 | 0.20 | 0.11 | 0.12 | 0.96 |
| Δ132 | 1.0 | 0.36 | 0.08 | 0.11 | 0.64 |
| Y246F | 0.48 | 0.33 | 0.52 | 0.45 | 0.32 |
| N278G | 1.4 | 0.79 | 0.69 | 0.81 | 0.92 |
| S173T | 0.82 | 1.14 | 0.85 | 0.85 | 0.94 |
| S346T | 0.98 | 1,6 | 0.74 | 0.79 | 0.32 |

*(Normalized affinity ratio = PositionX($A_{405}$H11.Y/$A_{405}$ H6.C6)/HPV11 ($A_{405}$H11.Y/$A_{405}$H6.C6)

TABLE 3

| | Antibody Binding Configurations | | | | |
|---|---|---|---|---|---|
| Position | H11.A3.2 | H11.B2 | H11.F1 | H11.G5 | H11.H3 |
| G131S | + | − | − | − | + |
| Y132Δ | + | −/+ | − | −/+ | + |
| Y246F | −/+ | −/+ | −/+ | −/+ | −/+ |
| N278G | + | +/− | +/− | +/− | +/− |
| S346T | + | + | + | + | − |

EXAMPLE 5

Stripping Assay

To monitor the production of HPV11 VLPs to insure that they contain the important neutralizing epitope, the following competition ELISA is employed. HPV6 derivative VLPs, but not HPV6 VLPs, compete for binding to HPV11 VLPs with monoclonal antibodies H11.B2, H11.F1, and H11.G5. This shows the presence of the neutralizing epitope on the VLPs by demonstrating specific, competable binding to the neutralizing epitope. The assay is performed in the following way.

1. Plate 10–100 ng of test batch HPV11 VLPs per well of a 96 well ELISA plate. Dilute sample in 1.0% BSA in PBS (ELISA buffer). Plate 50 μl sample. Incubate overnight at 4° C.

2. Remove supernatants from wells. Block for one hour with 5% powdered milk in PBS at room temperature.

3. Rinse with ELISA buffer.

4. Prepare dilutions of monoclonal antibody H11.F1

A. Prepare a set of dilutions with increasing amounts of HPV6 derivative VLPs.

B. Prepare a duplicate set of dilutions with increasing amounts of HPV6 VLPs.

C. Prepare a dilution with no VLPs added.

5. Add 50 μl of the antibody samples to the wells of the ELISA plate. Incubate for one hour at room temperature.

6. Remove antibodies and wash three times with ELISA buffer.

7. Add 50 μl of goat anti-mouse IgG (γ) at appropriate dilution. Incubate for one hour at room temperature.

8. Wash three times with ELISA buffer. Develop with an alkaline phosphatase assay and read at 405 nm.

9. A strong signal at 405 nm that is strongly competed with HPV6 derivative VLPs, but not HPV6 VLPs will verify the pressence of the neutralizing epitope on the test batch of HPV11 VLPs.

EXAMPLE 6

Monitoring Neutralization

HPV6 derivative VLPs are used to characterize test batches of polyclonal sera for neutralizing activity. A batch of polyclonal sera is generated, for example, by a test batch of HPV11 VLPs. Alternatively, it is a human sample for which a characterization of its neutralizing capability is desired.

A polyclonal sera is pre-cleared with HPV6 VLPs. This removes cross-reactive antibodies, both VLP dependent and non-dependent. The HPV11 neutralizing epitope is type 11 specific, and antibodies generated against it are not removed by pre-incubation with HPV6 VLPs. However, derivatized HPV6 particles bind these antibodies, and observation of such binding, in for example a standard ELISA, demonstrates the presence of neutralizing antibodies in the test sera sample.

A test sample of polyclonal sera is cleared according to the following procedure.

1. An estimate of the total VLP binding antibody is made. VLPs will be immobilized on an ELISA plate in sandwich format using an anti-HPV11 monoclonal (several are available). The amount of polyclonal antibody which binds is estimated using a second anti-HPV11 antibody of known concentration as a standard. Alternatively, the concentration of IgG of the polyclonal is determined and assumed to be all anti-HPV11.

2. HPV6 VLPs are added to an aliquot of sera in 10-fold µg excess to the amount of HPV11 antibody in the polyclonal sera, as determined in step one.

3. The mixture is incubated overnight at room temperature, followed by high speed centrifugation (300,000 g) for 5 hours to pellet the VLP-antibody complexes.

4. The procedure is repeated two more times.

5. The stripped sera is tested for binding in a sandwich ELISA. HPV6 and HPV6 derivative VLPs (which bind the neutralizing monoclonals) will be immobilised by an HPV6 monoclonal antibody. The stripped polyclonal sera should show only minimal binding to HPV6 VLPs. A strong signal against HPV6 derivitised VLPs demonstrates binding to the principal neutralizing domain of HPV11, and that the polyclonal sera contains neutralizing antibody.

A second assay may be established to demonstrate neutralizing capability in test sera sample using the Xenograph neutralization assay (Christensen et al., 1990. J. Virol. 64: 1936–1944; Christensen et al., 1994. J. Gen. Virol. 75: 2271–2276).

1. Stripped sera against HPV6 derivative VLPs are generated according to the protocol given above, substituting HPV6 derivative VLPs for HPV6 VLPs. Polyclonal sera stripped with HPV6 VLPs are made as a control.

2. A series of dilutions of the polyclonal sera are made and analyzed in the Xenograph neutralization assay to establish the neutralizing titer of the sera.

3. Parallel sets of dilutions of HPV6 derivative stripped and HPV6 stripped sera are made and titered in the Xenograph.

4. The presence of neutralizing activity in the Xenograph assay that is largely removed by stripping with HPV6 derivative VLPs, but not HPV6 VLPs, demonstrates by a biological assay the presence of antibodies in the sera against the HPV11 neutralising epitope.

EXAMPLE 7
Transient expression of VLPs in Sf9 cells

The HPV11 L1 structural gene was cloned from clinical isolates using the Polymerase Chain Reaction (PCR) with primers designed from the published L1 sequence (8,17). The CRPV L1 structural gene was cloned by PCR from viral genomic DNA. The L1 genes were subcloned into pVL1393 (Stratagene) for expression in Sf9 cells.

Sf9 cells were cotransfected using the BaculoGold Transfection kit (Pharmingen, San Diego, Calif.). Transfections were done according to the manufacturer's instructions with the following modification: $8 \cdot 10^6$ Sf9 cells were transfected in a 100 mm dish, with 4 µg of BaculoGold viral DNA and 6 ug of test plasmid DNA. Cells were harvested after 6 days, except where otherwise specified, and assayed for VLP production by Western Blot or ELISA assay (below).

EXAMPLE 8
Preparation of Sf9 extracts and ELISA assays.

Cells were harvested six days after transfection. Plates were scraped to resuspend cells, and the cells were collected by low speed centrifugation. Cells were resuspended in 300 µl of breaking buffer (1M NaCl, 0.2M Tris pH 7.6) and homogenized for 30 seconds on ice using a Polytron PT 1200 B with a PT-DA 1205/2-A probe (Brinkman) in a Falcon 2059 tube. Samples were spun at 2500 rpm in a GPR centrifuge (Beckman Instruments, Inc. Palo Alto, Calif.) for 3 minutes to pellet debris. Tubes were washed with an additional 150 µl of breaking buffer, supernatents collected in a 1.5 ml microfuge tube, and respun for 5 minutes in an Eppendorf microfuge (Brinkman). ELISA assays were begun the same day.

5 µl of extract was diluted into 50 µl of 1% BSA in phosphate-buffered saline solution (PBS), aliquoted onto a 96 well Immulon 2 microtiter plate (Dynatech Laboratories, Inc.), and incubated overnight at 4° C. Extracts were removed and the plate blocked with 5% powdered milk/PBS. All subsequent wash steps were performed with 1% BSA/PBS. The plate was incubated at room temperature with primary antibody for 1 hour. The primary antibodies, monoclonal antibodies CRPV.5A and H11.F1, were obtained as ascites stock from Dr. Neil Christensen. They are VLP-dependent and type specific antibodies which recognize CRPV and HPV11 VLPs respectively (Neil Christiansen, personal communication). They were diluted $10^5$-fold in 1% BSA/PBS before use. After washing in 1% BSA/PBS, plates were incubated for 1 hour with secondary antibody, peroxidase labeled Goat anti-Mouse IgG (g) (Kirkegaard & Perry Laboratories, Inc.) and used at $10^3$ dilution in 1% BSA in PBS. After a final washing, a horseradish peroxidase assay was performed and absorbance read at 405 nm.

EXAMPLE 9
Transfer of the HPV11 Neutralizing Epitope to HPV6

Based upon the studies in Example 4, we mutated the HPV6 L1 gene at amino acid residues 131, 245, and 277 to match the HPV11 L1 sequence. In addition, we inserted a tyrosine after residue 131, extending the length of the mutated HPV6 L1 gene by one residue to 501 amino acids. We designate this clone as HPV6:4. We predicted that these four changes, all of which match the HPV11 L1 sequence, would facilitate binding by HPV11 specific neutralizing antibodies H11.B2, H11.F1, and H11.G5. This is in fact true, as shown in the table below.

Relative Affinity Values to HPV6 and a Derivative

| Antibody | HPV6 | HPV6:4 |
|---|---|---|
| H11.A3 | 0.15 | 0.23 |
| H11.B2 | 0.18 | 0.82 |
| H11.F1 | 0.20 | 0.89 |
| H11.G5 | 0.14 | 0.84 |
| H11.H3 | 0.11 | 0.17 |

This validates that the four amino acid residues 131,132, 245, and 277 define the specificity of the binding site to neutralizing antibodies H11.B2, H11.F1, and H11.G5.

Antibody H11.H3 can be distinguished from the other three neutralizing antibodies by sensitivity to binding at position 346, and lack of sensitivity to binding at position 131. This indicates that the binding of this antibody has shifted towards the C-terminus, but still overlaps the binding site of the other three neutralizing monoclonal antibodies.

We further derivatized the HPV6 derivative clone defined above by adding an additional change at position 345, to match the sequence of HPV11 at its position 346. We designate this clone as HPV6:5. The prediction is that it will bind all four neutralizing antibodies, including H11.H3. The data is shown in the table below.

Relative Affinity Values to HPV6 and a Derivative

| Antibody | HPV6 | HPV6:5 |
|---|---|---|
| H11.A3 | 0.15 | 0.23 |
| H11.B2 | 0.18 | 0.82 |
| H11.F1 | 0.20 | 0.89 |
| H11.G5 | 0.14 | 0.84 |
| H11.H3 | 0.11 | 0.17 |

As expected, this clone produced VLPs which could bind neutralizing antibodies H11.B2, H11.F1, and H11.G5, and validates this observation. Unexpectedly, it did not bind antibody H11.H3 which indicates that an additional change to that at position 345 is also required for binding H11.H3.

EXAMPLE 10

Binding by neutralizing monoclonal antibody H11.H3.

To further study the binding of antibody H11.H3, a change is added at residue 438 of the HPV6 L1 gene, to match the residue of HPV11 L1 at 439. The change is added both to clone HPV6:4b (with changes at 132, 245, 277 and 345) as well as HPV6:5. This will generate clong HPV5b (132, 245, 277, 345 and 435) as well as HPV6:6. Clone HPV6:5b binds antibody H11.H3, and clone HPV6:6 binds antibodies H11.B2, H11.F1, H11.G5 and H11.H3. These clones exted the sensitivity obtainable in the assays outlined below in claims 2 and 3, and above in Examples 7 and 8.

EXAMPLE 11

To further study the binding of the neutralizing monoclonal antibodies, we back-mutated clone HPV6:4 at the four individual positions, and demonstrated that back-mutation only at residues 131 and 132 resulted in loss of binding. Generation of an additional HPV6 L1 clone with only these two changes, HPV6:2 demonstrated that these two changes alone are sufficient for binding the HPV11 neutralizing monoclonal antibodies. Thus, these studies collectively define the minimal epitope for the neutralizing antibodies.

What is claimed:

1. Synthetic virus-like particles generated from any of the following constructs:

a) HPV6:4, wherein HPV6 L1 gene has been mutated so that it encodes a protein wherein amino acid residues 131, 245, and 277 are the same as amino acid residues 131, 246, and 278 in HPV 11 L1 protein, and after amino acid residue 131 of HPV6 L1, a tyrosine residue has been inserted;

b) HPV6:5, which contain the same mutations as HPV6:4 and additionally has been further mutated so that it encodes a protein which, in addition to the mutations in a), amino acid residue 345 is the same as amino acid residue 346 in HPV11 L1 protein;

c) HPV6:2, wherein HPV6 L1 gene has been mutated so that it encodes a protein wherein amino acid 131 is the same as in HPV11 L1 protein, and additionally a tyrosine residue has been inserted as amino acid 132;

d) HPV6:4Δ132 which contains the same mutations as HPV6:4, except that there is no insertion of a tyrosine residue after amino acid 131; and e) HPV6:4,S131G which contains the same mutations as HPV6:4, except that amino acid residue 131 is glycine.

* * * * *